United States Patent [19]

Thorpe et al.

[11] 4,065,486

[45] Dec. 27, 1977

[54] PROCESS FOR RECOVERY OF PRODUCTS FROM A WASTE STREAM IN THE MANUFACTURE OF ACRYLONITRILE

[75] Inventors: John Anton Thorpe, Memphis, Tenn.; Harold Felton Porter, Hockessin, Del.

[73] Assignee: E. I. Du Pont de Nemours and Company, Wilmington, Del.

[21] Appl. No.: 722,514

[22] Filed: Sept. 13, 1976

[51] Int. Cl.$^2$ .................. C07C 120/14; C07C 120/00
[52] U.S. Cl. ............................. 260/465.3; 260/465.9
[58] Field of Search .......................... 260/465.3, 465.9

[56] References Cited

U.S. PATENT DOCUMENTS

| | | | |
|---|---|---|---|
| 2,904,580 | 9/1959 | Idoi, Jr. | 260/465.3 |
| 3,404,947 | 10/1968 | Miller et al. | 260/465.3 |
| 3,468,624 | 9/1969 | Miller et al. | 260/465.3 X |
| 3,876,508 | 4/1975 | Bonnema et al. | 260/465.3 X |
| 3,936,360 | 2/1976 | Wu | 260/465.9 X |

*Primary Examiner*—Joseph Paul Brust

[57] ABSTRACT

Process for recovering reactants and products e.g., acrylonitrile and hydrogen cyanide from an aqueous stream obtained in the ammoxidation of propylene which comprises heating an aqueous stream containing the afore-said compounds in a heat exchanger by circulating the stream at a velocity of at least 6 ft/sec through the exchanger while maintaining the stream in the liquid state to increase the temperature of the stream to at least 105° C and thereafter rapidly reducing the pressure of the heated stream sufficiently to vaporize 0.2–5% thereof and thereafter returning the vapor to the acrylonitrile process for recovery of energy used to heat the aqueous waste; usable materials e.g., acrylonitrile and hydrogen cyanide and compounds such as ammonia which can be used to neutralize acid streams and subsequently either incinerating the unvaporized material directly or using the unvaporized material as fertilizer after appropriate treatment.

7 Claims, 1 Drawing Figure

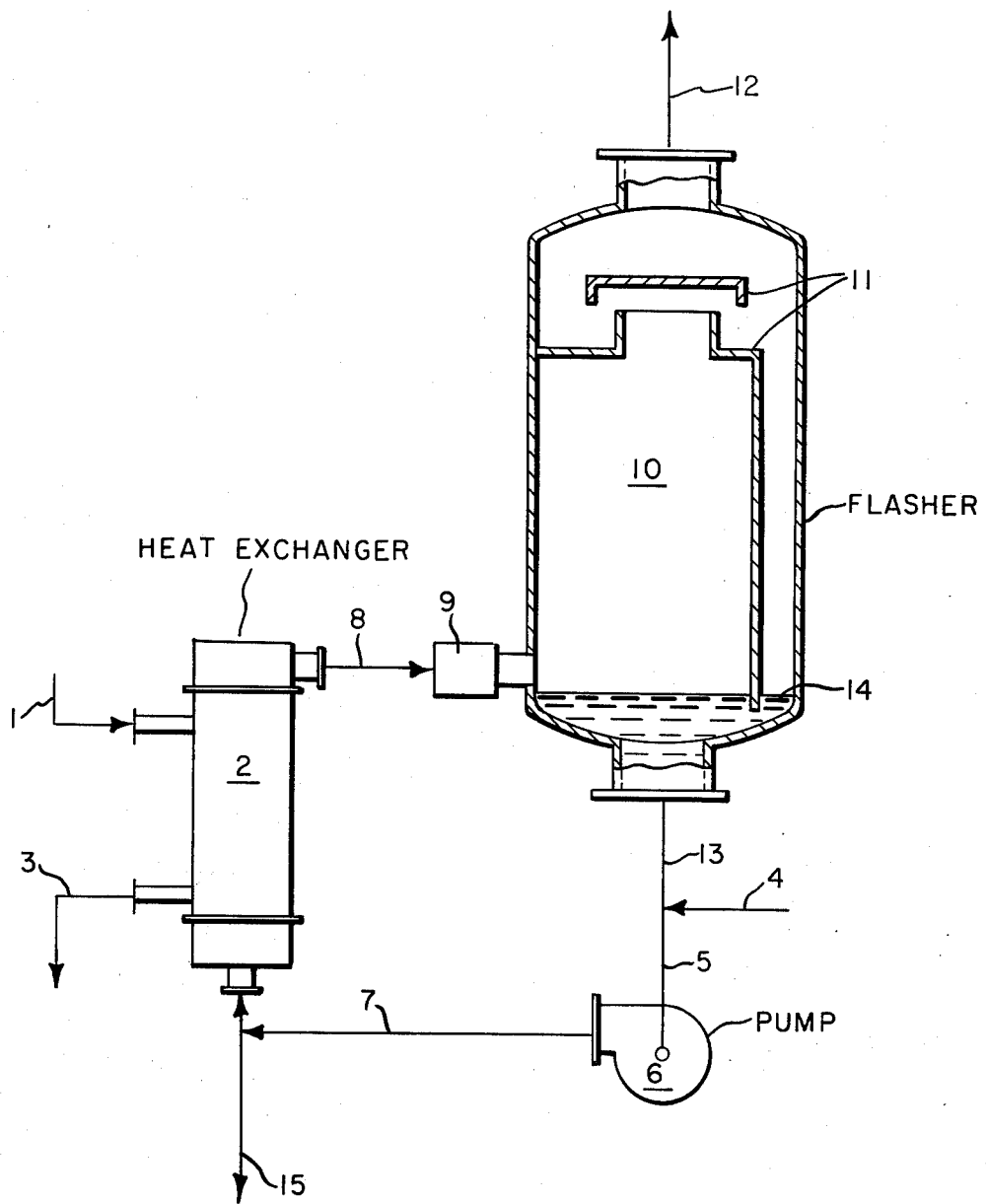

PROCESS FOR RECOVERY OF PRODUCTS FROM A WASTE STREAM IN THE MANUFACTURE OF ACRYLONITRILE

BACKGROUND OF THE INVENTION

1. Field of the Invention

The present invention is directed to a process for treating the aqueous waste from a process for the production of acrylonitrile by ammoxidation of propylene.

2. Description of the Prior Art

Typical processes for the preparation of acrylonitrile by the ammoxidation of propylene are described in U.S. Pat. Nos. 2,904,580; 3,876,508 and 3,936,360. These processes involve combining propylene, ammonia and air and passing that mixture over a suitable catalyst to produce acrylonitrile. The off gas from the reaction is initially directed to a cooling tower where the excess ammonia is neutralized with aqueous acid. Most of the desired products, e.g., acrylonitrile pass overhead through the cooling tower while the remaining products and by-products are absorbed in, or carried with, the aqueous solution exiting the base of the tower. This aqueous solution is then directed to a distillation column (waste water column) where most of the volatile materials, e.g., residual acrylonitrile and hydrogen cyanide are taken overhead. The tails from this distillation column, or waste water column, contain high boiling impurities, ammonium sulfate and reduced amounts of acrylonitrile, hydrogen cyanide and ammonia. This stream is particularly illustrated and described as the discharge through conduit 10 from column C of FIG. 1 in U.S. Pat. No. 3,876,508. Typically, this stream exhibits pH of 4.5–6.0 and contains (in percent by weight based on the total weight of the stream) 2–6% ammonium sulfate, 0.1–0.7% HCN as cyanohydrins, 0.01–0.5 acetonitrile, 0.01–.1% acrylonitrile, 0.001–.1% propionitrile, 0.001–0.05% acetaldehyde and 2.0–5.0% high boilers, e.g., nitriles such as fumaronitrile and higher molecular weight compounds such as polymers of acrylonitrile, acrolein and hydrogen cyanide. The remainder of the stream is essentially water.

The economical disposition of the aqueous waste stream from the above described acrylonitrile process has been extensively described in the art. Most of the processes are directed to the recovery of purified ammonium sulfate for use e.g., as a fertilizer. U.S. Pat. No. 3,711,597 discloses a process for the recovery of ammonium sulfate by adding nitric acid to a specific concentration and thereafter evaporating the resultant mixture at 40°–120° C following which ammonium sulfate is separated from the evaporated solution. U.S. Pat. No. 3,902,859 discloses the recovery of ammonium sulfate by concentrating the aqueous waste solution to the maximum degree possible while maintaining the salts in solution and thereafter adding an alcohol to precipitate the ammonium sulfate. U.S. Pat. No. 3,408,157 teaches the addition of mineral acid to the aqueous waste to precipitate heavy organics following which the material is filtered and the concentrate treated to precipitate relatively pure ammonium sulfate. U.S. Pat. No. 3,756,947 discloses a process for treating a waste water containing nitriles and cyanide by passing the waste through an activated sludge containing a specific form of bacteria. The removal of troublesome hydrogen cyanide from the waste stream by contacting with formaldehyde at a pH less than or equal to 3 is described in German Pat. No. 2,202,660. The waste stream has also been extracted with acetonitrile to remove organic matter prior to recovery of relatively pure ammonium sulfate as set forth in U.S. Pat. No. 3,607,136. Many prior techniques, for example, the process disclosed in U.S. Pat. No. 3,404,947, are concerned with disposing of the aqeuous waste stream by incineration. Alternate techniques for alleviating the substantial problem whereby this aqueous stream causes plugging of equipment when attempts are made to concentrate it involve the addition of ammonia or amines as disclosed in U.S. Pat. No. 3,468,624. More elaborate methods for treating the stream to recover ammonium sulfate are disclosed in British Patent No. 1,314,047 wherein complexing agents and a solvent such as dioxane, dimethylformamide or a lactam are added to the aqueous waste to prevent contamination of the crystallized ammonium sulfate.

None of the foregoing art discloses a process which permits the recovery of ammonium sulfate-organic containing solution which can be recovered for use as a fertilizer along with the recovery of a vapor stream containing unconsumed reactants such as ammonia which can be used elsewhere in the process and compounds such as acrylonitrile and hydrogen cyanide which can be recycled to the process.

SUMMARY OF THE INVENTION

The present invention provides a process for the recovery of reactants such as ammonia and products such as acrylonitrile from an aqueous stream from the waste water column of an acrylonitrile process as described hereinabove. The reactants and products along with ammonium sulfate are recovered by passing the stream through a heat exchanger at a velocity of at least 6 ft/sec usually at a velocity at a range 6–15 ft/sec and preferably at 8–10 ft/sec while maintaining the stream in the liquid state whereby the temperature of the stream is increased to at least 105° C, usually 120°–150° C and preferably 130°–135° C and thereafter rapidly reducing the pressure of the heated stream, e.g., by flashing to a degree sufficient to vaporize 0.2–5% by weight and preferably from 0.3–1.5% by weight. The pressure in the vaporizer is usually maintained in the range 0–25 psig and preferably in the range 10–15 psig. After the stream is vaporized the volatile material can be returned directly to the acrylonitrile process for recovery of certain reactants such as acrylonitrile and hydrogen cyanide as well as ammonia in a form suitable for neutralization of acid streams in the process while the unvaporized material can be incinerated directly or applied as a fertilizer after appropriate treatment.

THE DRAWING

A schematic representation of a typical apparatus for practicing the process of the present invention is shown in the drawing.

DETAILED DESCRIPTION OF THE INVENTION

The process of the present invention is practiced using the apparatus set forth in the FIGURE attached hereto and made a part of the specification. Steam is introduced via line 1 into heat exchanger 2 and condensate is removed from the heat exchanger via line 3. The aqueous waste stream is introduced into the apparatus via line 4 and thereafter directed via line 5 to pump 6 where it is pressurized and forced via line 7 through heat exchanger 2 and thence via line 8 through orifice 9. The hot stream under pressure is then introduced into flasher 10 which is equipped with an internal separating means comprising a column and hat portion identified as item 11. The vapor is withdrawn from the flasher via line 12 where it is subsequently treated to recover desirable products contained therein. The liquid bottoms are circulated through lines 13, 5 and 7 at a rate of at least 6 ft/sec through the heat exchanger 2. The circulation rate is maintained at a volume which is high relative to the amount of waste water introduced via line 4. The concentrated solution containing ammonium sulfate is removed continuously via line 15 so that a liquid level is maintained in flasher 10 at approximately location 14.

The temperature of the waste water exiting heat exchanger 2 via line 8 must be maintained at least 105° C to provide sufficient energy for vaporization and to prevent undesired precipitation of ammonium sulfate and/or high boilers and polymers contained in the aqueous solution. Usually the temperature of the stream exit the heat exchanger 2 is maintained in the range 120°–150° C and preferably in the range 130°–135° C.

In order to minimize fouling of heat exchanger it has been discovered that it is necessary to maintain a minimal velocity of liquid through the exchanger of at least 6 ft/sec and usually a velocity in the range 6–15 ft/sec. It is preferred to maintain a velocity through the heat exchanger in the range 8–10 ft/sec.

As would be apparent to one skilled in the art the degree of vaporization can be controlled by either the temperature of the stream entering flasher 10 or the pressure within flasher 10 relative to the entering stream. It is preferred to conduct the flasher at a pressure in the range 0–25 and preferably 10–15 psig in conjunction with the above discussed stream temperature, thus at least 30% of the entering stream (line 4) will be vaporized under the least severe conditions and as high as 95% can be vaporized by increasing the temperature and/or decreasing the pressure within flasher 10. It is preferred to vaporize between 80 and 95% of the stream (line 4) for optimum results.

The amount of material vaporized per pass through orifice 9 is maintained at a low level and the desired compounds can be removed with the vapor while the portion of the stream in the heat exchanger is maintained under liquid conditions which minimize fouling of the equipment.

The following examples are presented to illustrate but not to restrict the present invention. Parts and percentages are by weight unless otherwise noted.

EXAMPLE 1

A stream from a waste water column of an acrylonitrile plant was analyzed and found to contain 1.56% sulfate (2.15% ammonium sulfate as calculated from analyzed sulfate) 0.02% acetonitrile, 0.01% acrylonitrile, 0.05% propionitrile, 0.01% acetaldehyde and 0.36% hydrogen cyanide. pH of the stream was 5.0 and it contained 6.43% solids. The stream was fed to the apparatus described in FIG. 1 in which the flasher 10 was a cylindrical vessel 10 feet in diameter by 14 feet high which contained separator components as illustrated in the FIGURE. Two heat exchangers 2 and pumps 6 along with the associated piping were connected to flasher 10. Each heat exchanger 2 had an effective heat exchange area of 3,350 sq ft and each pump 6 had a capacity of 5,000 gallons/min. The above described feed stream was introduced via line 4 to each of the pumps 6 for a total feed rate to the apparatus of 40,500 pounds/hr. Steam via line 1 the heat exchanger was adjusted to maintain the exit solution via line 8 through orifice 9 and thence into flasher 10 at a temperature of 132°–134° C. After maintaining equilibrium and establishing the liquid level indicated at 14 in the flasher 10 while recirculating material via line 13, the overhead vapor rate via line 12 was measured to be 32,000 pounds/hr. The bottom flow removed from the system via line 15 was calculated by difference to be 8,500 pounds/hr. The average holdup time was 2.9 hours. The overhead vapors were analyzed and found to contain no sulfate, 0.09% ammonia, 0.02% acrylonitrile, 0.04% acetonitrile, 0.16% propionitrile, 0.01% acetaldehyde and 0.26% hydrogen cyanide and exhibited a pH of 6.0. The bottom flow exit line 15 was analyzed and found to contain 8.04% sulfate, 3.4% ammonia, 0.01% acetonitrile, 0.01% acrylonitrile, 0.07% propionitrile and 0.08% hydrogen cyanide and exhibited a pH of 4.7. Acetaldehyde was below detectable levels. The overhead vapor stream was returned to a suitable location in the acrylonitrile process and resulted in the recovery of ammonia (as an aqueous solution), acrylonitrile and hydrogen cyanide.

Extended operation as above described did not produce significant fouling or plugging of the apparatus.

EXAMPLES 2–13

Example 1 was repeated and the results are reported in Table 1. In each instance the vapors from flasher 3 were returned to the acrylonitrile process to recover the desired materials without adversely affecting the process operation.

As should be apparent from the foregoing examples hydrogen cyanide is obtained via the decomposition of cyanohydrins which is formed by the conditions of the concentrating operation especially by the extended holdup time in the flasher and circulating loops.

In addition to the above described advantages the reduction in volume occasioned by the concentrating reduces the cost of disposal of the waste.

TABLE

| | Flows (thousand lb/hr) | | | Separator Pressure (PSIG) | Vaporization | | Temperature (° C) | | Solution Hold-Up Time (Hrs.) |
| | | | | | % of Heater | | | | |
| Ex. | Feed (line 4) | Vapor (line 12) | Bottoms[1] (line 15) | | % of Feed (line 4) | Exit Flow (line 8) | Flasher | Exit Exchanger | |
| --- | --- | --- | --- | --- | --- | --- | --- | --- | --- |
| 2 | 51 | 15 | 36 | 14 | 29 | .3 | | | .7 |
| 3 | 47 | 19 | 28 | 7–8[2] | 40 | .4 | | | .9 |
| 4 | 30 | 19 | 11 | 7–8[2] | 63 | .4 | 115 | 127 | 2.3 |
| 5 | 43 | 18 | 25 | 7.5 | 42 | .4 | 115 | | 1.0 |
| 6 | 45 | 32 | 13 | 7 | 71 | .6 | 115 | | 1.9 |
| 7 | 42 | 30 | 12 | 13–14[2] | 71 | .6 | 123 | | 2.1 |
| 8 | 46 | 24 | 22 | 13–14[2] | 52 | .5 | 123 | | 1.1 |
| 9 | 51 | 33 | 18 | 13–14[2] | 65 | .7 | 125 | 133 | 1.4 |
| 10 | 43 | 28 | 15 | 13–14[2] | 65 | .6 | 125 | 132 | 1.7 |
| 11 | 43 | 29 | 14 | 13–14[2] | 67 | .6 | 124 | 132 | 1.8 |
| 12 | 40 | 31 | 9 | 13–14[2] | 78 | .6 | 125 | | 2.8 |

TABLE-continued

| | Flows (thousand lb/hr) | | | Separator Pressure (PSIG) | Vaporization | | Temperature (° C) | | Solution Hold-Up Time (Hrs.) |
| | | | | | % of Heater | | | | |
| Ex. | Feed (line 4) | Vapor (line 12) | Bottoms¹ (line 15) | | % of Feed (line 4) | Exit Flow (line 8) | Flasher | Exit Exchanger | |
|---|---|---|---|---|---|---|---|---|---|
| 13 | 40 | 31 | 9 | 13–14² | 78 | .6 | 125 | 132 | 2.8 |

¹By difference
²Estimated

I claim:

1. A process for the recovery of reactants and products contained in dilute aqueous stream from the waste water column of a process for the production of acrylonitrile by ammoxidation of propylene while concentrating said stream which reactants and products comprise hydrogen cyanide, acrylonitrile, ammonia, ammonium sulfate, and high boiling nitrogen containing impurities said process comprising mixing said dilute stream with a stream from the same source as said dilute stream partially concentrated by having a portion of the water removed therefrom passing the mixture obtained through a heat exchanger at a velocity of at least 6 ft/sec while maintaining said mixture in the liquid state to thereby heat the mixture to at least 105° C and thereafter rapidly reducing the pressure of the heated mixture sufficiently to vaporize a portion of said mixture and thereafter returning said vapor to said acrylonitrile process while withdrawing a portion of the unvaporized stream.

2. The process of claim 1 wherein the velocity is maintained in the range 6–15 ft/sec and the temperature is maintained in the range 120°–150° C.

3. The process of claim 2 wherein 0.2–5% of the heated mixture is vaporized upon each pass through said exchanger.

4. A process for concentrating a dilute aqueous waste stream comprising in percent by weight based upon the total weight of the stream hydrogen cyanide 0.1–0.7% (as cyanohydrins), 0.01–0.1% acrylonitrile, 2–6% ammonium sulfate 2.0–5.0% high boiling nitrogen containing impurities, 0.01–0.5% acetonitrile, and 0.001–0.05% acetaldehyde which process comprises introducing said stream into a circulating loop consisting essentially of a heat exchanger, a flasher and a circulating means wherein said loop contains a partially concentrated waste stream, obtained by passing said dilute stream through said heat exchanger and flasher thereby removing a portion of the water therefrom to form a mixture of said dilute and said partially concentrated waste stream, passing said mixture in the liquid state through a heat exchanger at a velocity of at least 6 ft/sec to thereby heat the mixture to at least 105° C and thereafter rapidly reducing the pressure of the heated mixture to vaporize at least 30% of the dilute aqueous waste introduced into said loop, recovering the vapor thus produced and withdrawing a portion of the partially concentrated waste stream while maintaining circulation through said loop.

5. The process of claim 4 wherein at least 90% of the dilute aqueous waste stream is vaporized.

6. The process of claim 4 wherein said mixture is heated to a temperature in the range 130°–135° C.

7. The process of claim 6 wherein 0.3–1.5% of said mixture is vaporized upon each passage through said exchanger.

* * * * *